United States Patent
Kirsch et al.

(10) Patent No.: US 8,414,612 B2
(45) Date of Patent: Apr. 9, 2013

(54) MULTIFILAMENT BARBED SUTURE

(75) Inventors: David Kirsch, Madison, CT (US); Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 278 days.

(21) Appl. No.: 12/941,283

(22) Filed: Nov. 8, 2010

(65) Prior Publication Data

US 2012/0116449 A1    May 10, 2012

(51) Int. Cl.
*A61B 17/04* (2006.01)

(52) U.S. Cl.
USPC .................................................. 606/228

(58) Field of Classification Search ............ 606/151, 606/228
See application file for complete search history.

(56) References Cited

U.S. PATENT DOCUMENTS

| | | | |
|---|---|---|---|
| 2,089,335 A * | 8/1937 | Brown | 140/92.2 |
| 3,123,077 A | 3/1964 | Alcamo | |
| 3,522,637 A * | 8/1970 | Brumlik | 24/445 |
| 4,024,871 A | 5/1977 | Stephenson | |
| 4,028,489 A * | 6/1977 | Berg et al. | 174/166 R |
| 5,123,913 A | 6/1992 | Wilk et al. | |
| 5,133,738 A | 7/1992 | Korthoff et al. | |
| 5,226,912 A | 7/1993 | Kaplan et al. | |
| 5,236,563 A | 8/1993 | Loh | |
| 5,342,376 A | 8/1994 | Ruff | |
| 5,569,302 A | 10/1996 | Proto et al. | |
| 5,683,417 A | 11/1997 | Cooper | |
| 5,695,879 A | 12/1997 | Goldmann et al. | |
| 5,814,056 A | 9/1998 | Prosst et al. | |
| 5,931,855 A | 8/1999 | Buncke | |
| 5,984,896 A * | 11/1999 | Boyd | 604/175 |
| 6,063,105 A | 5/2000 | Totakura | |
| 6,106,505 A | 8/2000 | Modak et al. | |
| 6,143,352 A | 11/2000 | Clark et al. | |
| 6,165,202 A | 12/2000 | Kokish et al. | |
| 6,203,564 B1 | 3/2001 | Hutton et al. | |
| 6,235,869 B1 | 5/2001 | Roby et al. | |
| 6,241,747 B1 | 6/2001 | Ruff | |
| 6,506,197 B1 | 1/2003 | Rollero et al. | |
| 6,562,051 B1 | 5/2003 | Bolduc et al. | |
| 6,599,310 B2 | 7/2003 | Leung et al. | |
| 6,620,846 B1 | 9/2003 | Jonn et al. | |
| 6,773,450 B2 | 8/2004 | Leung et al. | |
| 6,848,152 B2 | 2/2005 | Genova et al. | |

(Continued)

FOREIGN PATENT DOCUMENTS

| EP | 0 499 048 A1 | 8/1992 |
|---|---|---|
| EP | 0 632 999 A | 1/1995 |

(Continued)

OTHER PUBLICATIONS

European Search Report for European Application No. 10250002.2 dated Mar. 24, 2010. (9 pages).

(Continued)

*Primary Examiner* — Melanie Tyson
*Assistant Examiner* — Son Dang

(57) ABSTRACT

A surgical suture includes a plurality of intertwined unbarbed filaments defining a longitudinal axis and a barbed filament including an elongate body and a plurality of barbs disposed along a length thereof. The plurality of barbs extends radially outward from a surface of the elongate body, wherein the barbed filament at least partially intertwines with the plurality of unbarbed filaments.

20 Claims, 2 Drawing Sheets

U.S. PATENT DOCUMENTS

| | | |
|---|---|---|
| 6,881,766 B2 | 4/2005 | Hain |
| 7,056,331 B2 | 6/2006 | Kaplan et al. |
| 7,357,810 B2 | 4/2008 | Koyfman et al. |
| 7,371,253 B2 | 5/2008 | Leung et al. |
| 7,624,487 B2 | 12/2009 | Trull et al. |
| 2002/0077661 A1 | 6/2002 | Saadat |
| 2003/0149447 A1 | 8/2003 | Morency et al. |
| 2004/0010275 A1 | 1/2004 | Jacobs et al. |
| 2004/0039415 A1* | 2/2004 | Zamierowski ............... 606/215 |
| 2004/0060409 A1 | 4/2004 | Leung et al. |
| 2004/0060410 A1* | 4/2004 | Leung et al. ............. 83/522.14 |
| 2004/0088003 A1 | 5/2004 | Leung et al. |
| 2004/0153125 A1 | 8/2004 | Roby |
| 2005/0267531 A1 | 12/2005 | Ruff et al. |
| 2006/0079469 A1 | 4/2006 | Anderson et al. |
| 2006/0111734 A1 | 5/2006 | Kaplan et al. |
| 2006/0116718 A1 | 6/2006 | Leiboff |
| 2006/0135994 A1 | 6/2006 | Ruff et al. |
| 2007/0005110 A1* | 1/2007 | Collier et al. ............... 606/228 |
| 2007/0187861 A1 | 8/2007 | Genova |
| 2007/0257395 A1 | 11/2007 | Lindh |
| 2008/0082113 A1 | 4/2008 | Bishop |
| 2008/0195147 A1 | 8/2008 | Stopek |
| 2008/0221618 A1 | 9/2008 | Chen |
| 2008/0281357 A1 | 11/2008 | Sung |
| 2008/0312688 A1 | 12/2008 | Nawrocki |
| 2009/0018577 A1 | 1/2009 | Leung et al. |
| 2009/0105753 A1 | 4/2009 | Greenhalgh et al. |
| 2009/0140012 A1 | 6/2009 | Greer, Jr. |
| 2009/0210006 A1 | 8/2009 | Cohen et al. |
| 2009/0248066 A1 | 10/2009 | Wilkie |
| 2009/0287245 A1 | 11/2009 | Ostrovsky |
| 2010/0084780 A1 | 4/2010 | Lindh, Sr. |
| 2011/0046669 A1 | 2/2011 | Goraltchouk |
| 2011/0125188 A1 | 5/2011 | Goraltchouk |
| 2011/0288583 A1 | 11/2011 | Goraltchouk |
| 2012/0046675 A1 | 2/2012 | Bishop |

FOREIGN PATENT DOCUMENTS

| | | |
|---|---|---|
| EP | 0 647 452 A1 | 4/1995 |
| EP | 1 669 093 | 6/2006 |
| EP | 2 108 319 A1 | 10/2009 |
| EP | 2 133 028 A1 | 12/2009 |
| WO | WO 03/001979 A2 | 1/1993 |
| WO | WO 98/00065 | 1/1998 |
| WO | WO 98/52473 | 11/1998 |
| WO | WO 99/52451 A | 10/1999 |
| WO | WO 00/57933 | 10/2000 |
| WO | WO 01/52751 A | 7/2001 |
| WO | WO 2004/014236 A1 | 2/2004 |
| WO | WO 2004/030520 A2 | 4/2004 |
| WO | WO 2004/030704 A2 | 4/2004 |
| WO | WO 2004/030705 A2 | 4/2004 |
| WO | WO 2004/045663 A1 | 6/2004 |
| WO | WO 2004/066927 A2 | 8/2004 |
| WO | WO2007/131019 A2 | 11/2007 |
| WO | WO 2007/133103 A1 | 11/2007 |
| WO | WO 2008/042909 A2 | 4/2008 |
| WO | WO2008/042992 A2 | 4/2008 |
| WO | WO 2008/045375 A2 | 4/2008 |
| WO | WO 2008/107919 A1 | 9/2008 |
| WO | WO2008/112417 A2 | 9/2008 |
| WO | WO2008/141034 A1 | 11/2008 |
| WO | WO 2008/141034 A1 | 11/2008 |
| WO | WO2008/157142 A2 | 12/2008 |
| WO | WO 2009/105663 A2 | 8/2009 |
| WO | WO 2009/129251 A2 | 10/2009 |
| WO | WO2009/132284 A2 | 10/2009 |
| WO | WO2009/140012 A1 | 11/2009 |
| WO | WO 2011/025926 A1 | 3/2011 |

OTHER PUBLICATIONS

European Search Report for EP 11250756.1-2310 date of completion is Jan. 10, 2012 (3 pages).

George Odian, "Principles of Polymerization", Third Edition, pp. 569-573 (1991).

Robin R. Szarmach, et al., "An Innovative Surgical Suture and Needle Evaluation and Selection Program", Journal of Long-Term Effects of Medical Implants, 12(4), pp. 211-229 (2002).

European Search Report for EP 10177651.6-1526 date of completion is Dec. 14, 2010 (3 pages).

European Search Report EP 12 16 5912 dated Jul. 18, 2012.

European Search Report EP 12 16 9370 dated Sep. 12, 2012.

* cited by examiner

MULTIFILAMENT BARBED SUTURE

BACKGROUND

1. Technical Field

The present disclosure relates to a surgical suture and, more particularly, to an intertwined suture having one or more barbed filaments.

2. Background of Related Art

Sutures are commonly used to close wounds and surgical incisions. Sutures include monofilament sutures and braided sutures. Barbs may be created in monofilament sutures. A barbed suture includes an elongated body that has one or more spaced barbs, which project from the surface of the suture body along the body length. Barbed sutures offer several advantages for closing wounds and incisions. The barbs are arranged to allow passage of the barbed suture in one direction through tissue, but resist movement of the barbed suture in the opposite direction. Using barbed sutures enables the placement of tension in tissue with less slippage of the suture in the wound.

The number of suture barbs may be determined by the size of the wound and the strength required to hold the wound closed. In addition, depending on the specific application, wound, and length of time needed for wound healing, sutures with different material having different degradation rates may be used.

Monofilament barbed sutures are typically formed by making cuts or slits in the suture using a blade. As such, monofilament barbed sutures, however, may lack the required flexibility for a particular procedure being performed and may be prone to failure.

SUMMARY

In accordance with the present disclosure, a surgical suture includes a plurality of intertwined unbarbed filaments and one or more barbed filaments. The plurality of unbarbed filaments define a longitudinal axis. The barbed filament includes an elongate body and a plurality of barbs disposed along a length thereof. The plurality of barbs extend radially outward from the elongate body. The barbed filament at least partially intertwines with the plurality of unbarbed filaments.

In an embodiment, the barbed filament may be at least partially embedded within the plurality of intertwined unbarbed filaments. The barbed filament may be helically arranged along an outer surface of the plurality of intertwined unbarbed filaments. The plurality of barbs may be spatially separated along a length of the barbed filament.

In another embodiment, the barbed filament may include an absorbable material. The plurality of unbarbed filaments may also include an absorbable material. The plurality of unbarbed filaments may include a non-absorbable material. The barbed filament may include a non-absorbable material.

In yet another embodiment, the plurality of barbs may define an acute angle with respect to the elongate body of the barbed filament. The body of the barbed filament may include a first portion having a first plurality of barbs in a first direction and a second portion having a second plurality of barbs in a second direction, wherein the first and second directions may be opposite directions. The first and second portions of the elongate body of the barbed filament are intertwined with the plurality of intertwined unbarbed filaments adjacent proximal and distal portions of the plurality of intertwined unbarbed filaments, respectively.

In still yet another embodiment, the surgical suture may further include a second barbed filament. The second barbed filament may be at least partially embedded within the plurality of intertwined unbarbed filaments.

BRIEF DESCRIPTION OF THE DRAWINGS

The above and other objects and features of the present disclosure will become apparent from the following description of embodiments given in conjunction with the accompanying drawings, in which.

DETAILED DESCRIPTION

Figure 1:
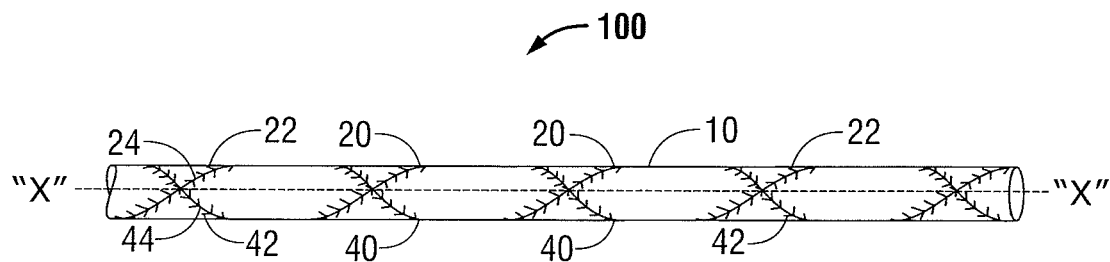
FIG. 1 is a perspective view of an intertwined suture in accordance with an embodiment of the present disclosure.

Various embodiments of the presently disclosed multifilament suture will now be described in detail with reference to the drawings, wherein like reference numerals identify similar or identical elements. In the drawings and in the description that follows, the term "proximal," will refer to the end of a device or system that is closer to the operator, while the term "distal" will refer to the end of the device or system that is farther from the operator. The term "intertwined" is used herein to mean braided, entangled, interlaced or comingled monofilaments or multifilaments.

Referring now to FIG. 1, an embodiment of the present disclosure is shown generally as an intertwined suture 100 defining a longitudinal axis "X-X." Intertwined suture 100 may be used to close wounds and surgical incisions. Intertwined suture 100 includes a plurality of intertwined unbarbed filaments 10 and a pair of barbed filaments 20, 40. Barbed filaments 20, 40 are woven intermittently around an outer surface of the plurality of unbarbed filaments 10. A standard braiding machine or a needle may be used to weave barbed filaments 20, 40 intermittently around the outer surface of the plurality of unbarbed filaments 10. With continued reference to FIG. 1, barbed filaments 20, 40 extend along substantially the entire length of intertwined suture 100. In particular, barbed filaments 20, 40 are helically woven around the outer surface of the plurality of intertwined unbarbed filaments 10. Alternatively, barbed filaments 20, 40 may be interwoven into the plurality of intertwined unbarbed filaments 10 through a use of a needle (not shown). In this manner, barbed filaments 20, 40 are securely intertwined with the plurality of unbarbed filaments 10.

With continued reference to FIG. 1, barbed filaments 20, 40 each include an elongate body 24, 44 and a plurality of barbs 22, 42 formed along the length of elongate body 24, 44. The plurality of barbs 22, 42 may be uniformly spaced or spatially separated along the length of barbed filaments 20, 40 and may extend radially outward from a surface of respective elongate bodies 24, 44. Barbs 22, 42 may be formed on, for example, smaller sized sutures, from 11-0 to 0 sized, through cuts made by a suitable cutting blade or lasers. For example, barbed sutures may be created through use of an ultrasonic cutting blade as disclosed by U.S. Patent Publication No. 2009/0210006, the entire contents of which are incorporated by reference herein. Alternatively, barbs 22, 42 may be made according to any method including, for example, injection molding, stamping or the like. Moreover, each barb 22, 42 may define an angle relative to respective bodies 24, 44 of barbed filaments 20, 40 to enable passage of intertwined suture 100 in one direction through tissue, but resist movement of suture 100 in the opposite direction. In particularly useful embodiments, the angle defined between the barb and the surface of the elongate body is <90°, or an acute angle.

Figure 2A:
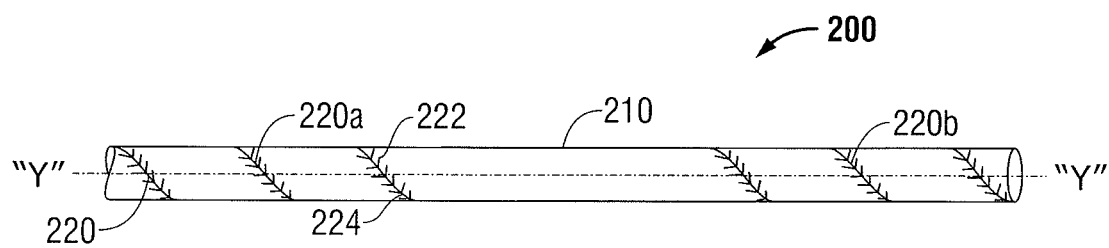
FIG. 2A is a perspective view of an intertwined suture in accordance with another embodiment of the present disclosure.

Turning now to FIG. 2A, an intertwined suture in accordance with another embodiment of the present disclosure is generally designated as an intertwined suture 200. Intertwined suture 200 is substantially similar to intertwined suture 100, and thus will only be described herein to the extent necessary to identify differences in construction and operation thereof. Throughout the following disclosure, like reference numeral will be used to identify like elements.

Intertwined suture 200 includes a plurality of intertwined unbarbed filaments 210 and a barbed filament 220 having a plurality of barbs 222. Intertwined suture 200 defines a longitudinal axis "Y-Y." Barbed filament 220 may be made with, various sized sutures described herein. In general, the diameter of the barbed filament 220 is less than the diameter of the intertwined suture 200. Barbed filament 220 is woven intermittently to an outer surface of the plurality of unbarbed filaments 210.

Barbed filament 220 includes an elongate body 224 and the plurality of barbs 222 along the length of elongate body 224. The plurality of barbs 222 may be uniformly spaced or spatially separated along the length of barbed filament 220 and may extend radially outward from a surface of elongate body 224. Barbs 222 may be formed on a monofilament suture through, for example, methods described herein. Each barb 222 may define an acute angle with respect to elongate body 224 of barbed filament 220 to enable passage of intertwined suture 200 in one direction through tissue, but resist movement of intertwined suture 200 in the opposite direction.

Figure 2B:
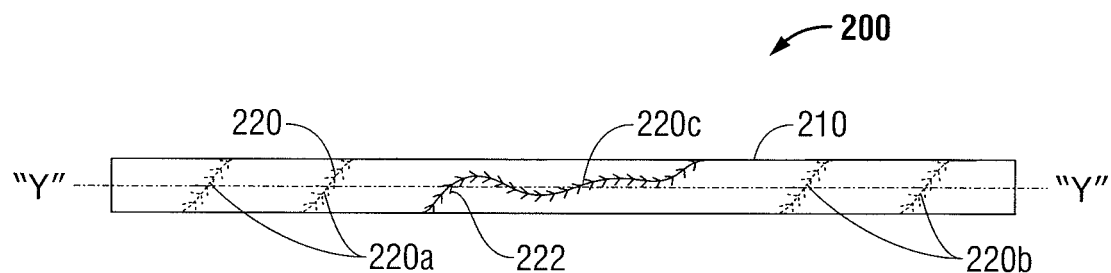
FIG. 2B is a longitudinal cross-sectional view of the intertwined suture of FIG. 2A.

As illustrated in FIG. 2B, barbed filament 220 extends along substantially the entire length of the plurality of intertwined unbarbed filaments 210. In particular, barbed filament 220 includes first and second body portions 220a, 220b (illustrated in phantom) helically woven around an outer surface of the plurality of intertwined unbarbed filaments 210 adjacent proximal and distal end portions of unbarbed filaments 210, respectively. Further, barbed filament 220 also includes a third body portion 220c embedded within the plurality of intertwined unbarbed filaments 210, as shown in FIG. 2B. First and second portions 220a and 220b are connected therebetween by the third portion 220c. The third portion is stitched through an interior portion of the suture 200 (as opposed to wrapped around the periphery of the suture). In other embodiments, the suture 200 may have a specific braid configuration to as to enable third portion 220c to be threaded or interwoven along an interior central portion of suture 200. In alternate embodiments, the third portion 220c may be unbarbed, connected first and second barbed portions 220a and 220b. Barbed configuration of the third portion 220c may facilitate suturing procedures by enabling the user to adjust, for example, the tension of suture 200. In addition, the third portion 220c of barbed filament 220 may better secure barbed filament 220 to the plurality of unbarbed filaments 210. Barbed filament 220 may be woven intermittently to the outer surface of the plurality of intertwined unbarbed filaments 210 through a use of a needle (not shown).

Figure 3A:
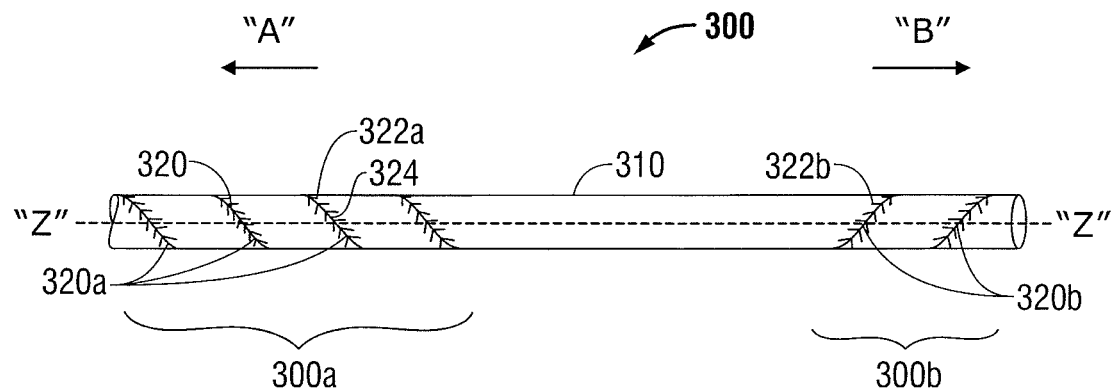
FIG. 3A is a perspective view of an intertwined suture in accordance with still another embodiment of the present disclosure.

Turning now to FIG. 3A, an intertwined suture in accordance with another embodiment of the present disclosure is generally designated as an intertwined suture 300. Intertwined suture 300 is substantially similar to intertwined suture 200, and thus will only be described herein to the extent necessary to identify differences in construction and operation thereof. Throughout the following disclosure, like reference numeral will be used to identify like elements.

Intertwined suture 300 includes a plurality of intertwined unbarbed filaments 310 and a barbed filament 320 having a plurality of barbs 322a, 322b. Intertwined suture 300 defines a longitudinal axis "Z-Z." Barbed filament 320 is woven intermittently to an outer surface of the plurality of unbarbed filaments 310. Barbed filaments 320 may be made with, for example, smaller sized diameter sutures. More specifically, the diameter of the barbed filament 320 is less than/smaller than the diameter of the intertwined suture 300. Barbs 322a, 322b may be formed on a monofilament suture through, for example, methods described herein.

Barbed filament 320 includes an elongate body 324 and the plurality of barbs 322a, 322b along the length of elongate body 324. The plurality of barbs 322a, 322b may be uniformly spaced or spatially separated along the length of barbed filament 320 and may extend radially outward from a surface of elongate body 324. Each barb 322a, 322b may define an acute angle with respect to elongate body 324 of barbed filament 320 to enable passage of intertwined suture 300 in a preferred direction through tissue.

Figure 3B:
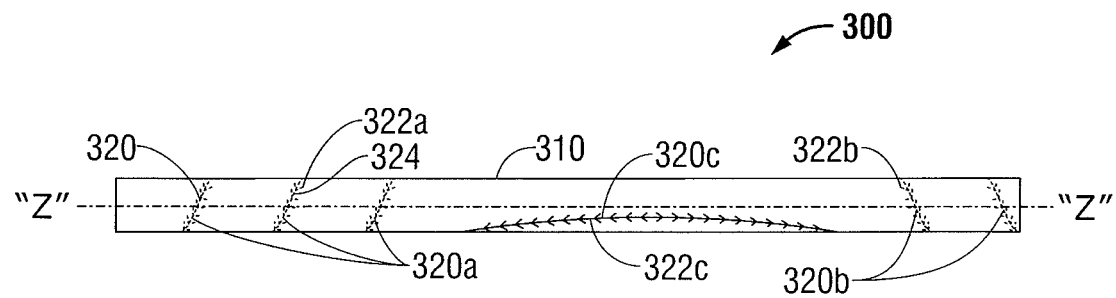
FIG. 3B is a longitudinal cross-sectional view of the intertwined suture of FIG. 3A.

Barbed filament 320 extends along substantially the entire length of the plurality of intertwined unbarbed filaments 310. Barbed filament 320 is at least partially embedded within an interior portion of the intertwined suture 300. In particular, barbed filament 320 includes first and second body portions 320a, 320b helically woven around the outer surface of the plurality of intertwined unbarbed filaments 310 adjacent proximal and distal end portions of unbarbed filaments 310, respectively. Barbed filament 320 further includes a third body portion 320c that is embedded in the plurality of intertwined unbarbed filaments 310. In some embodiments, the third portion may be barbed or unbarbed. Barbs 322c disposed on third portion 320c of barbed filament 320 are intertwined within the plurality of intertwined unbarbed filaments 310 and as such, do not extend radially from the outer surface of the plurality of unbarbed filaments 310, as best shown in FIG. 3B. The third portion 320c is disposed within the outer surface of the suture 310. Such configuration may facilitate suturing procedures by enabling the user to adjust, for example, the tension of suture 300. In addition, the embedded third portion 320c may better secure barbed filament 320 to the plurality of unbarbed filaments 310.

In particular, a first plurality of barbs 322a enable movement of a first portion 300a of intertwined suture 300 through the tissue in a first direction as indicated by arrow "A". Additionally, movement of the first plurality of barbs 322a prevents movement of the first portion 300a relative to the tissue in a direction opposite first direction "A." Similarly, a second plurality of barbs 322b enable movement of a second portion 300b of intertwined suture 300 through the tissue in a second direction as indicated by arrow "B". Further, movement of the second plurality of barbs 322b prevents movement of the second portion 300b relative to the tissue in the direction opposite the second direction "B."

It is also envisioned that the plurality of barbs 322a, 322b need not be embedded partially along the longitudinal axis of intertwined suture 300. Rather, barbed filament 320 may include barbs 322a, 322b only at first and second portions 320a, 320b of barbed filament 320. In this manner, barbed filament 320 may be helically woven along substantially the entire length of intertwined suture 300. However, third portion 320 having barbs 322c embedded in the plurality of unbarbed filaments 310 may better secure barbed filament 320 to the plurality of unbarbed filaments 310.

It is also envisioned that any suitable arrangement or braiding pattern of barbed filaments 20, 40, 220, 320 with respect to unbarbed filaments 10, 210, 310 may be chosen. While barbed filaments 20, 40, 220, 320 have been illustrated as being arranged in a helical pattern on an outer surface of unbarbed filaments 10, 210, 310 barbed filaments 20, 220, 320 may be arranged in any suitable pattern. Moreover, the number, configuration, spacing and surface area of barbs 22, 42, 222, 322a, 322b can vary depending upon the tissue, in which the suture is used, as well as the composition and geometry of the material utilized to form the suture. The proportion of barbs 22, 42, 222, 322a, 322b may remain relatively constant while the overall length of the barbs and the spacing of the barbs may be determined by the tissue being connected. For example, if the suture is to be used to penetrate and connect a relatively firm tissue, the barbs may be made relatively short and more rigid to facilitate entry into this rather firm tissue. However, if the suture is intended for use in a soft tissue, the barbs may be made longer and spaced farther apart to increase the ability of the suture to grip the soft tissue.

Polymers possessing shape memory properties which may be used to construct sutures disclosed herein include, for example, synthetic materials, natural materials (e.g., biological) and combinations thereof, which may be biodegradable and/or non-biodegradable. As used herein, the term "biodegradable" includes both bioabsorbable and bioresorbable materials. By biodegradable, it is meant that the materials decompose, or lose structural integrity under body conditions (e.g., enzymatic degradation, hydrolysis) or are broken down (physically or chemically) under physiologic conditions in the body (e.g., dissolution) such that the degradation products are excretable or absorbable by the body.

Intertwined sutures 100, 200, 300 made from a biodegradable material maintain their structural integrity after implantation for a predetermined period of time, depending on the characteristics of the particular copolymer used. It is further contemplated that a bioactive agent may be impregnated within a polymer utilized to form an intertwined suture 100, 200, 300 or applied to the surface thereof. Suitable bioactive agents include, for example, biocidal agents, antibiotics, antimicrobial agents, medicants, growth factors, anti-clotting agents, analgesics, anesthetics, anti-inflammatory agents, wound repair agents and the like, and combinations thereof.

Suitable biodegradable polymers include, but are not limited to, aliphatic polyesters; polyamides; polyamines; polyalkylene oxalates; poly(anhydrides); polyamidoesters; copoly(ether-esters); poly(carbonates) including tyrosine derived carbonates; poly(hydroxyalkanoates) such as poly(hydroxybutyric acid), poly(hydroxyvaleric acid), and poly(hydroxybutyrate); polyimide carbonates; poly(imino carbonates) such as poly(bisphenol A-iminocarbonate and the like); polyorthoesters; polyoxaesters including those containing amine groups; polyphosphazenes; poly(propylene fumarates); polyurethanes; polymer drugs such as polydiflunisol, polyaspirin, and protein therapeutics; biologically modified (e.g., protein, peptide) bioabsorbable polymers; and copolymers, block copolymers, random copolymers, homopolymers, blends, and combinations thereof.

Suitable non-degradable materials include, but are not limited to, polyolefins such as polyethylene (including ultra high molecular weight polyethylene) and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polytetramethylene ether glycol; polybutesters, including copolymers of butylene terephthalate and polytetramethylene ether glycol; 1,4-butanediol; polyurethanes; acrylic polymers; methacrylics; vinyl halide polymers and copolymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; copolymers of vinyl monomers with each other and olefins such as ethylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof. Additionally, non-biodegradable polymers and monomers may be combined with each other.

It is further envisioned that barbed filaments 20, 40, 220, 320 may be formed of shape memory polymeric materials which are capable of adopting a shape in vivo suitable for adhering tissue or affixing a surgical device to tissue. Shape memory polymeric materials utilized to form a barbed filament of the present disclosure possess a permanent shape and a temporary shape. In embodiments, the temporary shape is of a configuration which enhances the ability for the surgeon to introduce a multifilament barbed suture into tissue. The permanent shape, which is assumed in vivo upon application of energy, such as heat or light, is of a configuration which enhances the retention of, for example, a surgical mesh in tissue and/or adhesion of a surgical device to tissue.

Shape memory polymers are a class of polymers that, when formed into an object such as a barbed suture, can be temporarily deformed by mechanical force and then caused to revert back to an original shape when stimulated by energy. Shape memory polymers exhibit shape memory properties by virtue of at least two phase separated microdomains in their microstructure. The first domain is composed of hard, covalently cross-linked or otherwise chain motion-limiting structures, which act as anchors to retain the object's original shape. The second domain is a switchable soft structure, which can be deformed and then fixed to obtain a secondary or temporary shape.

It should also be noted that sutures described herein may comprise various cross-sectional shapes and geometries. Suitable cross-sectional shapes include, but are not limited to, oval, elliptical, square, rectangular, trapezoidal, triangular, and polygonal.

Additionally, the suture may include biologically acceptable additives such as plasticizers, antioxidants, dyes, dilutants, bioactive agents and combinations thereof, which can be coated on the filaments or fibers, or impregnated into the fibers or filaments (e.g. during compounding or extrusion) used to form the suture of the present disclosure.

Further, sutures of the present disclosure may comprise a needle disposed on at least one end thereof. Suitable needles include those within the purview of those skilled in the art.

It will be understood that various modifications may be made to the embodiments disclosed herein. Therefore, the above description should not be construed as limiting, but merely exemplifications of embodiments. Those skilled in the art will envision other modification within the scope and spirit of the claims appended thereto.

What is claimed is:

1. A surgical suture comprising:
   a plurality of intertwined unbarbed filaments defining a longitudinal axis; and
   a barbed filament including an elongate body and a plurality of barbs disposed along a length thereof, the plurality of barbs extending radially outward from a surface of the elongate body, wherein the barbed filament at least partially intertwines with the plurality of unbarbed filaments, at least a portion of the barbed filament helically arranged along an outer surface of the plurality of intertwined unbarbed filaments.

2. The surgical suture according to claim 1, wherein the barbed filament is at least partially embedded within the plurality of intertwined unbarbed filaments.

3. The surgical suture according to claim 1, wherein the plurality of barbs are spatially separated along a length of the barbed filament.

4. The surgical suture according to claim 1, wherein the barbed filament includes an absorbable material.

5. The surgical suture according to claim 1, wherein the plurality of unbarbed filaments include an absorbable material.

6. The surgical suture according to claim 1, wherein the plurality of unbarbed filaments include a non-absorbable material.

7. The surgical suture according to claim 1, wherein the barbed filament includes a non-absorbable material.

8. The surgical suture according to claim 1, wherein the plurality of barbs define an acute angle with respect to the elongate body of the barbed filament.

9. The surgical suture according to claim 1, wherein the elongate body of the barbed filament includes a first portion having a first plurality of barbs in a first direction and a second portion having a second plurality of barbs in a second direction, wherein the first and second directions are opposite directions.

10. The surgical suture according to claim 9, wherein the first and second portions of the elongate body of the barbed filament are intertwined with the plurality of intertwined unbarbed filaments adjacent proximal and distal portions of the plurality of intertwined unbarbed filaments, respectively.

11. The surgical suture according to claim 1, further comprising at least a second barbed filament.

12. The surgical suture according to claim 11, wherein the second barbed filament is at least partially embedded within the plurality of intertwined unbarbed filaments.

13. A surgical suture comprising:
    a plurality of intertwined unbarbed filaments defining a longitudinal axis; and
    first and second barbed filaments each including an elongate body and a plurality of barbs disposed along a length thereof, the plurality of barbs extending radially outward from a surface of the elongate body, wherein the first barbed filament is at least partially intertwined with the plurality of unbarbed filaments, and the second barbed filament is at least partially embedded within the plurality of intertwined unbarbed filaments.

14. The surgical suture according to claim 13, wherein the first barbed filament is at least partially embedded within the plurality of intertwined unbarbed filaments.

15. The surgical suture according to claim 13, wherein at least a portion of at least one of the first and second barbed filaments is helically arranged along an outer surface of the plurality of intertwined unbarbed filaments.

16. The surgical suture according to claim 13, wherein at least one of the first or second barbed filament includes an absorbable material.

17. The surgical suture according to claim 13, wherein at least one of the plurality of unbarbed filaments includes an absorbable material.

18. The surgical suture according to claim 13, wherein at least one of the plurality of unbarbed filaments includes a non-absorbable material.

19. The surgical suture according to claim 13, wherein at least one of the first or second barbed filament includes a non-absorbable material.

20. The surgical suture according to claim 13, wherein at least one of the first or second barbed filament includes a first portion having a first plurality of barbs in a first direction and a second portion having a second plurality of barbs in a second direction, wherein the first and second directions are opposite directions.

* * * * *